US007399751B2

(12) United States Patent
Kirkpatrick et al.

(10) Patent No.: US 7,399,751 B2
(45) Date of Patent: Jul. 15, 2008

(54) PRODUCTION OF A BIOLOGICAL FACTOR AND CREATION OF AN IMMUNOLOGICALLY PRIVILEGED ENVIRONMENT USING GENETICALLY ALTERED SERTOLI CELLS

(75) Inventors: Shaun A. Kirkpatrick, Tucson, AZ (US); Paul Gores, Charlotte, NC (US); Craig Halberstadt, Charlotte, NC (US)

(73) Assignee: Sertoli Technologies, Inc., Tucson, AZ (US)

( * ) Notice: Subject to any disclaimer, the term of this patent is extended or adjusted under 35 U.S.C. 154(b) by 76 days.

(21) Appl. No.: 10/219,804

(22) Filed: Aug. 15, 2002

(65) Prior Publication Data

US 2002/0192200 A1 Dec. 19, 2002

Related U.S. Application Data

(62) Division of application No. 09/433,429, filed on Nov. 4, 1999, now abandoned.

(51) Int. Cl.
*A61K 31/711* (2006.01)
(52) U.S. Cl. .......................... 514/44; 424/93.21; 800/18
(58) Field of Classification Search .............. 435/320.1, 435/325, 455
See application file for complete search history.

(56) References Cited

U.S. PATENT DOCUMENTS

| | | | |
|---|---|---|---|
| 5,082,670 A | 1/1992 | Gage et al. | |
| 5,236,838 A | 8/1993 | Rasmussen et al. | |
| 5,399,346 A | 3/1995 | Anderson et al. | |
| 5,451,660 A | 9/1995 | Builder et al. | |
| 5,521,070 A * | 5/1996 | Meulien .................... | 435/69.1 |
| 5,591,625 A | 1/1997 | Gerson et al. | |
| 5,633,150 A | 5/1997 | Wood et al. | |
| 5,663,304 A | 9/1997 | Builder et al. | |
| 5,702,700 A | 12/1997 | Sanberg et al. | |
| 5,725,854 A | 3/1998 | Selawry | |
| 5,759,534 A * | 6/1998 | Selawry .................... | 424/93.7 |
| 5,759,536 A | 6/1998 | Bellgrau et al. | |
| 5,830,460 A | 11/1998 | Sanberg et al. | |
| 5,849,285 A | 12/1998 | Selawry | |
| 5,958,404 A | 9/1999 | Selawry | |
| 5,969,211 A | 10/1999 | Burns et al. | |
| 2004/0086494 A1 | 5/2004 | John | |

FOREIGN PATENT DOCUMENTS

| | | |
|---|---|---|
| EP | 0 260 148 A2 * | 3/1988 |
| WO | WO 95/32627 | 12/1995 |
| WO | WO 95/28167 | 3/2005 |
| WO | WO 2005/018540 | 3/2005 |

OTHER PUBLICATIONS

Ciotti et al. Evidence for Overlapping Active Aites for 17alpha Ethynlestradiol and Bilirubin in the Human Major Bilirubin UDPglucoronosyltransferase Biochemistry 35:101 19-10124, 1996.*

Ciotti et al. Evidence for Overlapping Active Aites for 17alpha Ethynlestradiol and Bilirubin in the Human Major Bilirubin☐☐UDpglucoronosyltransferase Biochemistry 35:101 19-10124, 1996.*

Verma et al., Nature, vol. 389, 1997, pp. 239-242.*

Anderson, Nature, vol. 392, 1998, pp. 25-30.*

Juengst, Brit. Med. J., vol. 326, pp. 1410-1411.*

MacGregor G.R. et al., "Construction of Plasmids that Express *E.coli* -Galactosidase in Mammalian Cells", 17(6):2365 (1989), XP-000032246.

Okayama H. et al., "A cDNA Cloning Vector that Permits Expression of cDNA Inserts in Mammalian Cells", *Molecular & Cellular Biology* 3(2):280-289 (1983), XP-008020929.

Groskreutz D. et al., "CAT Reporter Systems: New pCAT® 3 Reporter Vectors and Antibodies Provide Increased Expression and Detection Capabilities", *Promega Notes Magazine* 55(2):1-7 (1996), XP-002278388.

Muramatsu T. et al., "Foreign Gene Expression in the Mouse Testis by Localized In Vivo Gene Transfer", *Biochemical and Biophysical Research Communications* 233(1):45-49 (1997), XP-002099972.

Seppen J. et al., "Transplantation of Gunn Rats with Autologous Fibroblasts Expressing Bilirubin UDP-Glucuronosyltransferase: Correction of Genetic Deficiency and Tumor Formation", *Human Gene Therapy* 8(1):27-36 (1997), XP-009030118.

(Continued)

*Primary Examiner*—James Ketter
(74) *Attorney, Agent, or Firm*—Finnegan, Henderson, Farabow, Garrett & Dunner LLP

(57) ABSTRACT

The present invention provides a method of providing an individual with a biological factor or intermediate thereof which comprises introducing into the individual Sertoli cells genetically altered to produce the biological factor or intermediate thereof. The genetically altered Sertoli cells are administered in an amount effective to produce the desired effect. Aside from producing the biological factor or intermediate thereof, the engineered Sertoli cells also create an immunologically privileged site. Vectors comprising a promoter which functions in Sertoli cells operably linked to coding sequence for a desired biological factor are also provided as are Sertoli cells comprising such vectors. A pharmaceutical composition comprising Sertoli cells genetically altered to produce a biological factor is also provided.

18 Claims, No Drawings

OTHER PUBLICATIONS

Wang L. et al., "A Factor IX-Deficient Mouse Model for Hemophilia B Gene Therapy", *Proc. Natl. Acad. Sci. USA* 94(21):11563-11566 (1997), XP-002278403.

Korbutt G.S. et al., "Cotransplantation of Allogeneic Islets with Allogeneic Testicular Cell Aggregates Allows Long-Term Graft Survival Without Systemic Immunosuppression", *Diabetes* 46:317-322 (1997), XP-002962502.

Ducray A. et al., "Establishment of a Mouse Sertoli Cell Line Producing Rat Androgen-Binding Protein (ABP)", *Steroids* 63(5-6):285-287 (1998), XP-004132212.

Blanchard et al., Adenovirus-Mediated Gene Transfer to Rat Testis in Vivo. Biology of Reproduction. 1997, vol. 56, pp. 495-500.

Dufour et al., "Transgenic Sertoli Cells as a Vehicle for Gene Therapy", *Cell Transplantation*, 13:1-6 (2004).

Gage, F., "Cell Therapy", *Nature*, 392:18-24 (1998).

Guidance for Industry: Source Animal, Product, Preclinical, and Clinical Issues Concerning the Use of Xenotransplantation Products in Humans, Final Guidance, *U.S. Department of Health and Human Services Food and Drug Administration Center for Biologics Evaluation and Research (CBER)*, dated Apr. 2003.

Guttenbach et al., "Cytogenic characterization of the TM4 mouse Sertoli cell line. I. Conventional banding techniques, FISH and SKY", *Cytogenet Cell Genet*, 94:71-78 (2001).

Hohmeier et al., "Islets for all?", *Nature Biotechnology*, 23:1231-1232 (2005).

Mather, J., "Establishment and Characterization of Two Distinct Mouse Testicular Epithelial Cell Lines", *Biology of Reproduction*, 23:243-252 (1980).

McClure et al., "Constitutive Fas Ligand Gene Transcription in Sertoli Cells Is Regulated by Sp1", *The Journal of Biological Chemistry*, 274(12):7756-7762 (1999).

Sun et al., "The Minimal Set of Genetic Alterations Required by Conversion of Primary Human Fibroblasts to Cancer Cells in the Subrenal Capsule Assay", *Neoplasia*, 7(6):585-593 (2005).

On-Line Medical Dictionary, "Primary cell", <http://cancerweb.ncl.ac.uk/omd/>, Mar. 6, 1998.

U.S. Appl. No. 08/726,531, filed Oct. 7, 1996, John, Constance M.

U.S. Appl. No. 09/131,501, filed Aug. 9, 1998, Hall, Deborah E.

Al-Hendy, et al., Correction of the Growth Defect in Dwarf Mice with Nonautologous Microencapsulated Myoblasts—An Alternate Approach to Somatic Gene Therapy, *Human Gene Therapy* 6: 165-175, 1995.

Arenas, E., et al., Neurotrophin-3 prevents the death of adult central noradrenergic neurons in vivo, *Nature* 367: 368-371, 1994.

Bramson J., et al., The use of adenoviral vectors for gene therapy and gene transfer in vivo, *Current Opinion in Biotechnol.* 6: 590-595, 1995.

Cheng, J., et al., Protection from Fas-Mediated Apoptosis by a Soluble Form of the Fas Molecule, *Science* 263(5154): 1759-1762, 1994.

Chervonsky, A., et al., The Role of Fas in Autoimmune Diabetes, *Cell* 89: 17-24, 1997.

Connelly, S., et al., Sustained Expression of Therapeutic Levels of Human Factor VIII in Mice, *Blood* 87: 4671-4677, 1966.

Crystal, R., Transfer of Genes to Humans: Early Lessons and Obstacles to Success, *Science* 270(5235): 404-410, 1995.

Culver, K., et al., Lymphocytes as cellular vehicles for gene therapy in mouse and man, *Proc. Nat. Acad. Sci. USA* 88: 3155-3159, 1991.

Del Cerro, M., et al., Transplantation of Y79 Cells Into Rat Eyes: an In Vivo Model of Human Retinoblastomas, *Invest. Opthalmol. Vis. Sci.* 34: 3336-3346, 1993.

Docherty, K., Gene therapy for diabetes mellitus, *Clin. Sci.* 92: 321-330, 1997.

Dong, H., et al, Challenges for Gene Therapy of Type 1 Diabetes, *Current Gene Therapy* 2: 403-414, 2002.

Dufour, J. et al., Biology of Reproduction, 64:S1-272 (2001).

Dufour, J., et al., Genetically engineered Sertoli cells are able to survive allogeneic transplantation, *Gene Therapy* 11: 694-700 (2004).

Dufour, J., et al., Transgenic Sertoli Cells as a Vehicle for Gene Therapy, *Cell Transplantation* 13: 1-6 (2004).

Ebendal, T., et al., Engineering cells to secrete growth factors, *J. Neurol.* 241: S5-S7, 1994.

Ebert, K., et al., A Moloney MLV-Rat Somatotropin Fusion Gene Produces Biologically Active Somatotropin in a Transgenic Pig, *Mol. Endocrinol.* 2(3): 277-283, 1988.

Fallaux, F., et al., Gene therapy for the hemophilias, *Current Opinion in Hematology* 3: 385-389, 1996.

Flotte, T., et al., Adeno-associated Virus Vector Gene Expression Occurs in Nondividing Cells in the Absence of Vector DNA Integration, *Am J. Respir. Cell Mol. Biol.* 121: 517-521, 1994.

Flotte, T., et al., Stable in vivo expression of the cystic fibrosis transmembrane conductance regulator with an adeno-associated virus vector, *Proc. Natl. Acad. Sci. USA* 90: 10613-10617, 1993.

Freese, A., et al., Prospects for Gene Therapy in Parkinson's Disease, *Movement Disorders* 11: 469-488, 1996.

Guillou, F., et al, Sertoli Cell-specific Expression of the Human Transferrin Gene, *The Journal of Biological Chemistry* 266(15): 9876-9884, 1991.

Hadjantonakis, A., et al., Generating green fluorescent mice by germline transmission of green fluorescent ES cells, *Mechanisms of Development* 76: 79-90 (1998).

Hallek, M., et al., Recombinant adeno-associated virus (rAAV) vectors for somatic gene therapy: recent advances and potential clinical applications, *Cytokines and Molecular Therapy* 2: 69-79, 1996.

Hammer, R., et al., Genetic Engineering of Mammalian Embryos, *J. Anim. Sci.* 63: 269-278, 1986.

Hortelano, G., et al., Delivery of Human Factor IX in Mice by Encapsulated Recombinant Myoblasts: A Novel Approach Towards Allogeneic Gene Therapy of Hemophilia B, *Blood* 87(12): 5095-5103, 1996.

Houdebine, L., Production of pharmaceutical proteins from transgenic animals, *J. of Biotechnology*. 34: 269-287, 1994.

Hoyer, L., et al., Production of Human Therapeutic Proteins in Transgenic Animals, *Vox Sanguinis 67 Supplement* 3: 217-220, 1994.

Hughes M., et al., Delivery of a Secretable Adenosine Deaminase Through Microcapsules-A Novel Approach to Somatic Gene Therapy, *Human Gene Therapy* 5: 1445-1455, 1994.

International Preliminary Report on Patentability for Application No. PCT/US04/21462 issued Jul. 27, 2006.

International Search Report for Application No. PCT/US04/21462 mailed Jul. 7, 2006.

JAX Data Sheet (http://jaxmice.jax.org/strain/003115.html, accessed Apr. 11, 2007).

Kappel, C., et al., Regulating gene expression in transgenic animals, *Curr. Opinion Bio*. 3: 548-553, 1992.

Lau, H., et al., Prevention of Islet Allograft Rejection with Engineered Myoblasts Expressing FasL in Mice, *Science* 273(5271):109-112, 1996.

Lipshultz, L., et al., Characterization of Human Sertoli Cells in Vitro, *J. Clin. Endocrin. Metab*. 55(2): 228-237, 1982.

Martinez-Serrano, A., et al., Protection of the Neostriatum against Excitotoxic Damage by Neurotrophin-Producing, Genetically Modified Neural Stem Cells, *Journal of Neuroscience* 16(15): 4604-4616, 1996.

Mitanchez, D., et al., Glucose-Stimulated Genes and Prospects of Gene Therapy for Type 1 Diabetes, *Endocrine Reviews* 18(4): 520-540, 1997.

Mountz, J., et al., Production of Transgenic Mice and Application of Immunology and Autoimmunity, *Am. J. Med. Sci*. 300: 322-329, 1990.

Mullins, L., et al., Perspectives Series: Molecular Medicine in Genetically Engineered Animals, *J. Clin. Invest*. 98(11): Supplement:S37-S40, 1996.

Nelson, S., et al., Characterization of the Functional Properties and Nuclear Binding Proteins of the Rat Luteinizing Hormone/Chorionic Gonadotropin Receptor Promoter in Leydig Cells, *Endocrinology* 135(5): 1729-1739, 1994.

Orkin, S., et al., Report and Recommendations of the Panel to Assess the NIH Investment in Research on Gene Therapy, 1-38, Dec. 7, 1995.

Paquis-Flucklinger, V., et al., Expression in transgenic mice of the large T antigen of polyomavirus induces Sertoli cell tumors and allows the establishment of differentiated cell lines, *Oncogene* 8: 2087-2094, 1993.

Press Release from Titan Pharmaceuticals, Inc., *Business Newswire* May 1996.

Roitt, I., et al., *Immunology, Second Edition, J.B. Lippincott*, pp. 3.08-3.10 (1989).

Romano, G., et al., Latest Developments in Gene Transfer Technology: Achievements, Perspectives, and Controversies over Therapeutic Applications, *Stem Cells* 18: 19-39, 2000.

Roth, E., et al, Nonviral Transfer of the Gene Encoding Coagulation Factor VIII in Patients with Severe Hemophilia A, *New England Journal of Medicine* 344(23): 1735-1742 (2001).

Sakuragawa, N., et al., Immunostaining of Human Amniotic Epithelial Cells: Possible Use as a Transgene Carrier in Gene Therapy for Inborn Errors of Metabolism, *Cell Transplantation* 4(3): 343-346, 1995.

Seigel, G., Gene replacement therapy in the CNS: A view from the retina, *Behavorial and Brain Sciences* 18: 69, 1995.

Shimada, T., Current status and future prospects of human gene therapy, *Acta Paediatrica Japonica* 38: 176-181, 1996.

Stedman's Medical Dictionary, 26th Edition, (1995).

Tiedge, M., et al., Gene Therapy of Diabetes Mellitus—Aims, Methods and Future Prospects, *Exper. Clin. Endocrinol. & Diabetes* 103: 46-55, 1995.

Uckert, W., et al., Retrovirus-Mediated Gene Transfer in Cancer Therapy, *Pharmac. Ther.* 63: 323-345, 1994.

Wall, R.J., Transgenic Livestock: Progress and Prospects for the Future, *Thenogenology* 45: 57-68, 1996.

Weatherall D.J., Scope and limitations of gene therapy, *British Med. Bull.* 51(1): 1-11, 1995.

Wickelgren, I., Muscling Transplants Into Mice, *Science* 273(5271): 33, 1996.

Written Opinion of the International Searching Authority for Application No. PCT/US04/21462 mailed Jul. 7, 2006.

Dufour, J., "Genetically engineered Sertoli cells as a vehicle for gene therapy," *Xenotransplantation*, 2007; 14(5):548-549.

Palu, G., *In pursuit of new developments for gene therapy of human diseases*, J. of Biotech., 68: 1-13 (1999).

Cole et al., *Transplantation of microcapsules (a potential bio-artificial organ): biocompatibility and host reaction*, J. of Materials Science: Materials in Medicine, 4:437-442 (1993).

Sundstrom et al., *Experimental testicular teratoma promotes formation of humoral immune responses in the host testis*, J. of Reproductive Immunology, 42:107-126, (1999).

Ritter et al., *Cloning of Two Human Liver Bilirubin UDP-glucuronosyl-transferase cDNAs with Expression in COS-1 Cells*, J. of Biological Chemistry, 266:1043-1047 (1991).

Jiang, C., *Cloning and characterization of the 5'flanking region of the stem cell factor gene in rat Sertoli cells*, Gene, 185:285-290 (1997).

Eskola, V., *Stable transfection of the rat follicle-stimulating hormone receptor complementary DNA into an immortalized murine Sertoli cell line*, Mol. and Cell. Endocrinology, 139:143-152 (1998).

\* cited by examiner

PRODUCTION OF A BIOLOGICAL FACTOR AND CREATION OF AN IMMUNOLOGICALLY PRIVILEGED ENVIRONMENT USING GENETICALLY ALTERED SERTOLI CELLS

CROSS REFERENCE TO RELATED APPLICATIONS

The present application is a divisional of application Ser. No. 09/433,429 filed Nov. 4, 1999 now abandoned.

FIELD OF THE INVENTION

Transplants of healthy organs or cells into a patient suffering from a disease are often rejected by the body due to an immune response initiated in response to the foreign tissue or cells. Genetically altered cells administered during gene therapy are often met with a similar immune response. The present invention provides a method of cellular transplantation in which an immunologically privileged site is created, thus alleviating the rejection associated with conventional transplantation and gene therapies.

Specifically, the present invention provides compositions and methods for providing an individual with a biological factor or intermediate thereof which comprises introducing into the individual a therapeutically effective amount of Sertoli cells genetically manipulated to produce the biological factor or intermediate thereof and wherein the Sertoli cells create an immunologically privileged site. A pharmaceutical composition comprising genetically altered Sertoli cells which produce a biological factor is also provided.

BACKGROUND OF THE INVENTION

Certain chronic diseases destroy the functional cells in affected organs. Individuals with such diseases are often unable to produce proteins or other biological products necessary to maintain homeostasis and usually require numerous exogenous substances to survive. Transplanting healthy organs or cells into an individual suffering from such a disease may be necessary to save the individual's life. This type of therapy is generally regarded as a last alternative to curing an otherwise fatal condition. Such transplants, however, are often rejected by the body due to an immune response initiated in response to the foreign tissue or cells. Presently, the only recourse to combat this immune response is to administer chronic nonspecific immunosuppression agents. The use of nonspecific immunosuppression agents however, is fraught with unwanted side effects such as increased susceptibility to infection, hypertension, renal failure and tumor growth.

In the fields of cell and organ transplantation, Selawry et al., have demonstrated that Sertoli cells can be used to create an artificial privileged environment when isolated from the testes and then transplanted into heterologous sites. Privileged environments have been created using both allogeneic and xenogeneic Sertoli cells. Rajotte and Korbutt, 1997 *Diabetes* 46: 317-322. Similarly, both rat Sertoli cell allografts and porcine Sertoli cell xenografts have been shown to survive for at least two months in the rat brain without cyclosporin A immunosuppression. Saporta, S. et al., 1997 *Exp. Neurology* 146(2):299-304. Selawry, et al., have also demonstrated the immunoprotection of islet cells placed in the rat kidney capsule when cotransplanted with Sertoli cells. Long term islet survival and functional recovery in a diabetic rat model have been demonstrated. Selawry, H., et al., 1993 *Cell Transplant* 2:123-129. It has recently been suggested that Sertoli cells express an immunosuppressant factor, Fas ligand (Fas-L), responsible all or in part for providing the testis with its immunoprivileged status. Sandberg, P. R., et al., 1997 *Cell Transplantation* 6(2):191-193; Saporta, S., et al., supra.

Immune rejection of genetically altered cells during gene therapy also remains a problem. In order to overcome the problem, autologous cells, i.e., a patient's own cells, may be used. In fact, most of the currently approved human gene therapy protocols depend on genetic alteration of autologous cells. Such cells however, may be difficult to obtain due to the diseased state of the patient and are often destroyed during harvesting. Those cells that survive harvesting are often difficult to grow in vitro and require complicated culture conditions and purification methodologies.

There is a need, therefore, for compositions and methods for producing a biological factor in a subject wherein cells which are genetically altered to produce the biological factor are readily available and more easily manipulated in vitro. In addition, the need exists for compositions and methods for producing a biological factor in a subject who receives allogeneic or xenopeneic cells which do not trigger an immune response requiring chronic immunosuppression.

SUMMARY OF THE INVENTION

The present invention provides compositions and methods for providing an individual with a biological factor or intermediate thereof which comprises introducing into the individual a therapeutically effective amount of Sertoli cells genetically manipulated Lo produce the biological factor or intermediate thereof and wherein the Sertoli cells create an immunologically privileged site.

The present invention also provides a method of treating a disease that results from a deficiency of a biological factor which comprises administering to a subject in need of such treatment a therapeutically effective amount of Sertoli cells genetically transformed to produce the biological factor or an intermediate of the biological factor and wherein the Sertoli cells create an immunologically privileged site.

Preferably, the genetically altered Sertoli cells are administered by transplantation. Transplantation may be by xenograft or allograft.

The present invention also provides a pharmaceutical composition comprising Sertoli cells genetically transformed to produce a biological factor or intermediate thereof admixed with a pharmaceutically acceptable carrier.

Also provided is a compartmentalized kit comprising a first container adapted to contain Sertoli cells genetically altered to produce a biological factor or intermediate thereof.

A vector comprising in the 5' to 3' direction a promoter which functions in Sertoli cells operatively linked to a coding sequence for a biological factor or intermediate is also provided by the present invention. The vector may further comprise a 3' termination sequence which functions in Sertoli cells and/or a signal sequence coding for a signal peptide. The signal sequence is located downstream from the promoter sequence and upstream to the coding sequence for a biological factor or intermediate.

Sertoli cells comprising the subject vectors are also provided.

DETAILED DESCRIPTION OF THE INVENTION

The present invention provides compositions and methods for producing a biological factor in a subject. The compositions and methods protect themselves from immune destruction by the subject, thereby eliminating the need for chronic immunosuppression.

In accordance with the present invention, Sertoli cells, the predominant cells of male testes, are used to produce a biological factor such as a protein in vivo. The Sertoli cells used to produce the biological factor are genetically altered and are generated by either ex vivo gene transfer or else isolated from a transgenic animal that expresses the biological factor in Sertoli cells. The genetically altered Sertoli cells are then introduced into a subject so that the biological factor is produced in that subject. The resultant transplanted Sertoli cells, in addition to producing a desired biological factor, also create an immunoprivileged environment at the site of transplantation.

Preferably, the route of introduction is by subcutaneous transplantation into such sites as the renal subcapsular space, subcutaneous facie, liver subcapsular space, brain, hepatic portal vein or omental pouch. The genetically altered Sertoli cells may also be placed in a biocompatible device that allows for contact with the vascular system, localizes the Sertoli cells, and enables the Sertoli cells to survive long term. Such a device also provides added protection from rejection by the immune system. An example of such a biocompatible device is described in U.S. Pat. No. 5,182,111, issued to Aebischer et al. Immuno-isolation devices such as alginate or thermoplastic capsules and hollow fibers may also house the genetically altered cells in vivo. Such devices are reviewed in Chang, P. L. 1997 *IEEE Engineering in Medicine and Biology*, September/October, pp. 145-151.

In accordance with the present invention, a transgenic animal that expresses a biological factor in Sertoli cells can be made using any number of currently available systems. For example, expression constructs having a promoter which functions in Sertoli cells operably linked to coding sequence for a biological factor or intermediate can used to transfect the testes of living mice by microparticle bombardment and electroporation. Muramatsu T. et al., (1997) *Biochem. and Biophys. Res. Commun.* 233(1):45-49. Such constructs may also be microinjected into pronuclei by means of standard procedures as described in Hogan et al. (1986) *Manipulating the Mouse Embryo: a Laboratory Manual*, Cold Spring Harbor Laboratory Press, New York.

The present invention is useful in improving the general health, well being, or appearance of an individual by supplying a therapeutically effective amount of a biological factor or intermediate thereof or else is useful in treating a disease that results from a deficiency of a biological factor.

As defined by the present invention, a biological factor is a protein or nonprotein compound that is necessary for cellular metabolism and homeostasis. Further in accordance with the present invention, a biological factor is a protein or nonprotein compound that is absent, deficient or altered in a subject suffering from a particular disease. As used herein, the term "protein" includes but is not limited to peptides and polypeptides. The biological factor may be a protein which enhances the immunosuppressive and growth enhancing properties of Sertoli cells. When the biological factor is a nonprotein compound, the Sertoli cells are genetically engineered to produce a protein such as an enzyme which protein is necessary for one or more steps in the biosynthetic pathway of a nonprotein compound. Thus, the Sertoli cells may be engineered to produce a protein intermediate to a nonprotein biological factor.

Recombinantly produced proteins of the Sertoli cells may comprise any number of structural, therapeutic or biologically functional proteins i.e., a polypeptide or protein which affects the cellular mechanism of the cell in which the biologically functional protein is expressed or to which it is administered. For example, the biologically functional protein may be a protein which affects the cellular mechanism of the Sertoli cell in which the biologically functional protein is expressed. The biologically functional protein can also be a protein which improves the health of a mammal by either supplying a missing protein, by providing increased quantities of a protein which is underproduced in the mammal, or by providing a protein which inhibits or counteracts an undesired molecule which may be present in the mammal. The biological factor may also be a factor which helps maintain or improves the health and well being of the individual and includes for example, peptides which stimulate or decrease appetite.

The biologically functional protein can be a protein which is essential for normal growth or repair of cells. The biologically functional protein may also be one which is useful in fighting diseases such as cancer, atherosclerosis, sickle-cell anemia and the thalassemias. Examples of such biologically functional proteins are hemoglobin ($\alpha$, $\beta$ or $\gamma$-globin), hematopoietic growth factors such as granulocyte-macrophage colony stimulating factor (GM-CSF), macrophage colony stimulating factor (M-CSF) and erythropoietin (EPO). Another example is tumor necrosis factor (TNF), which is a molecule that can be used to treat cancer, and in particular, tumors. The tumor suppressor p53 and retinoblastoma (RB) are also contemplated. Various cytokines such as mast cell growth factor (MGF) and interleukins 1-11 are also proteins which are contemplated for production by the genetically altered Sertoli cells of the present invention. Factor XIII (for treatment of hemophilia A), Factor IX (for treatment of hemophilia B), IL-2 (for enhancing the Sertoli cell's ability to provide immunoprotection), insulin (for treatment of diabetes), and dopamine (for treatment of Parkinson's disease) are also examples of proteins which can be produced by the Sertoli cells in accordance with the present invention.

B-UGT is yet another example of a protein which can be made by the subject genetically altered Sertoli cells for the treatment for Crigler-Najjar (CN) disease. Mammals normally have a liver enzyme, bilirubin UDP-glucuronosyltransferase (B-UGT), which conjugates bilirubin (an end product of the hemoglobin breakdown) with glucuronic acid, rendering the molecule more water soluble and excretable. Patients with Crigler-Najjar (CN) disease have a deficiency in B-UGT and accumulate high serum levels of bilirubin. Gunn rats are also incapable of bilirubin conjugation due to a genetic defect in UDP-glucuronyl transferase. Gunn rat fibroblasts expressing recombinant B-UGT have been transplanted intraperitonealy into Gunn rats with resultant correction of the genetic defect.

Thus, any protein which can be produced through recombinant DNA means is contemplated for production by the subject genetically altered Sertoli cells and for use in the methods of the present invention. Many well known procedures exist for the preparation of DNA sequences which code for a desired protein. For example, oligonucleotides of various lengths can be synthesized by known procedures. Several such oligonucleotides can be assembled into longer, double stranded molecules. Alternatively, DNA molecules having the desired coding sequences can be synthesized by use of the enzyme reverse transcriptase using messenger RNA related to the desired polypeptide as a template for the action of reverse transcriptase (cDNA cloning). Another possibility for preparing DNA sequences coding for the desired protein is the cloning of genomic DNA fragments obtained from a gene bank or library. In many instances, the DNA encoding the protein of interest is commercially available.

In some instances, the recombinantly produced protein is beneficial in exerting its effect on the Sertoli cell in which it is produced. IL2 is an example of such a protein. In most other instances however, the recombinantly produced protein of the genetically altered Sertoli cell benefits the subject only when such protein reaches other non-Sertoli cells. Thus, in a preferred embodiment of the invention, the recombinantly produced protein is exported across the Sertoli cell membrane and outside the Sertoli cell, i.e., secreted. In this aspect of the invention, the recombinantly produced protein will have on its N-terminal end a signal peptide (N-terminal leader sequence). The signal peptide enables the transport of the recombinantly produced protein out of the Sertoli cell where it is produced and into the intercellular spaces and capillaries of the surrounding cells. Once transported out of the Sertoli cell, the recombinantly produced protein enters the circulatory system of the subject.

The signal peptide may be encoded by the same gene from which the promoter is derived, e.g., FSHR. In this embodiment of the invention, the recombinantly produced protein is most often a chimeric protein. The native signal peptide of the recombinantly produced protein may also used. In yet another embodiment, the signal peptide may be from a protein other than the recombinantly produced protein or protein whose corresponding gene provides the promoter for the expression vector. Many different proteins have signal peptides at their N-terminal ends. The skilled artisan is aware of many different sequences known as signal sequences, which code for signal peptides. Such signal sequences are useful for incorporation into expression vectors of the present invention in order to ensure secretion of the recombinantly produced protein out of the Sertoli cell.

Sertoli cells which are to be genetically altered to produce a desired biological factor are first isolated using methods known in the art such as those described in Cheng et al., 1987 *J. Biol. Chem.* 26:12768-12779. Sertoli cells can be separated from other testicular cells such as Leydig cells, peritubular cells and germ cells, using conventional techniques. For example, the testes of a male mammal, such as a human, mouse, rat, pig, boar or ram, are first collected by castration. The testes are then chopped into several pieces and subsequently washed by centrifugation.

Testicular Leydig cells can be removed from the tissue suspension using digestion agents such as trypsin and DNase. The remaining cell suspension is then washed by centrifugation several times. The pellet is resuspended in collagenase, incubated and washed by centrifugation to eliminate peritubular cells within the testes. Testicular germ cells can be removed by incubating the pellet with hyaluronidase and DNase. After several washings by centrifugation, the Sertoli cells can be collected for genetic transformation. Similar methods of isolating Sertoli cells are described in Selawry, H. P. and Cameron, D. F.,(1993) *Cell Transplantation* 2:123-129; and Korbutt, G. S., et al, (1997) *Diabetes* 46:317-322.

Established Sertoli cell lines may also be used to produce a biological factor in accordance with the present invention. For example, an immortalized rat Sertoli cell line (SerW3) has been established. Pognan, F., et al., 1997 *Cell Biology and Toxicology* 13:453-463. Fresh primary rat Sertoli cells were immortalized with the T antigens of the Simian virus (SV40) which are known to immortalize heterologous cells but not transform them. The SerW3 Sertoli cell line has structural and biochemical properties similar to those of primary cells in culture or Sertoli cells in testicular sections. Pognan F., supra. A prepubertal rat Sertoli cell line known as 93RS2 has also recently been developed. Jiang, C., et al., 1997 *J. Andrology* 18(4):393-399. Conditionally immortalized Sertoli cells lines have also been established from H-2K $^{b}$-tsA58 transgenic mice. Walther N., et al., 1996 *Exp. Cell Res.* 225:411-421.

In accordance with the present invention, either primary or cultured Sertoli cells may be used to produce a biological factor. Whether primary cells or cultured cells, the Sertoli cells of the present invention may be obtained from species such as rat, human, porcine, murine, bovine or other species. These distantly related Sertoli cells function as "universal" biological factor producing cells since upon administration, such cells will not trigger an immune rejection, even in a distantly related or non related recipient subject.

In accordance with the present invention, the isolated Sertoli cells may be genetically altered to produce a desired biological factor using any number of well known methods. For example, a DNA or RNA sequence coding for a particular protein is first placed within a vector which can replicate within a Sertoli cell. Thus, the present invention also provides vectors for expression of proteins in the Sertoli cell. Within the vector, coding sequence for a particular protein is operably linked at its 5' end to a promoter which functions in human, mouse, rat, pig, boar or ram cells, including Sertoli cells. In a preferred embodiment, the vector also contains a 3' termination sequence operably linked to the 3' end of the coding sequence.

The vectors of the present invention can be constructed by standard techniques known to one of ordinary skill in the art and found, for example, in Sambrook et al. (1989) *Molecular Cloning: A Laboratory Manual*, Cold Spring Harbor Laboratory Press, New York, or any of a myriad of laboratory manuals on recombinant DNA technology that are widely available. A variety of strategies are available for ligating fragments of DNA, the choice of which depends on the nature of the termini of the DNA fragments and can be readily determined by the skilled artisan.

The vectors of the present invention may also contain other sequence elements to facilitate vector propagation, isolation and subcloning; for example, selectable marker genes and origins of replication that allow for propagation and selection in bacteria and host cells. Selectable marker genes can include ampicillin and tetracycline resistance genes for propagation in bacteria or neomycin, hygromycin or zeocin resistance for selection in mammalian cells. Sequences for heterologous genes coding for structural, therapeutic or biologically functional proteins as well as sequences for selectable markers and reporter genes are well known to the skilled artisan. Examples of reporter genes include GFP, luciferase, CAT, and β-galactosidase. By "heterologous genes" is meant coding sequences or parts thereof which are artificially introduced into Sertoli cells.

Inducible expression systems are presently available where exogenously administered factors function to induce gene expression. Such systems are especially useful in selection of Sertoli cells which have been transformed with an expression vector of the present invention. The REV TET-ON™ and REV TET-OFF™ systems available from Clonetech Laboratories, Palo Alto, Calif., and the Ecdysone-Inducible Mammalian Expression System, available from Invitrogen, Carlsbad, Calif., are especially helpful in this regard.

Promoters which function in Sertoli cells are known to those of skill in the art. For example, the promoter for transferrin or clusterin may be used. In order to limit the expression of the desired biological factor or intermediate to Sertoli cells only, the follicle stimulating hormone receptor (FSHR) promoter may be employed. Other promoters, upstream 5' regulatory sequences and 3' regulatory sequences including termination sequences which may be used in the vectors of the present invention include sequences from Cytomegalo virus (CMV), Simian Virus 40 (SV40), the Moloney Murine Leukemia (MOMLV) virus, Herpes-virus, pox-virus, and Adeno-associated virus (AAV), Epstein-Barr virus (EBV).

The clusterin gene has been studied in mouse, rat, and human. Herault et al., 1992 *Nucleic Acids Research* 20:6377-6383; Wong et al., 1993 *J. Biol. Chen.* 268:5021-5031, Wong et al., 1994 *Eur. J. Biochem.* 221:917-925; Jordan-Starck et al., 1994, *J. Lipid Res.* 35: 194-210; Rosemblit and Chen, 1994 *J. Mo. Endocrinology* 13: 69-76. The gene is expressed in the male reproductive tissues at different levels and is most highly expressed in the Sertoli cells. Rosemblit et al., 1996 *J. Mol. Endocrinology* 16:287-296. It has been found in rat and mouse that androgens and cAMP negatively regulate clusterin gene expression. Pignataro et al., 1992 *Endocrinology* 130(5):2745-2750. Clusterin regulatory sequences such as the promoter and 5' flanking sequences from rat have been identified as located between nucleotides −266 and +54. Potential negative regulatory DNA elements may be present at upstream locations such as −266 to −714 and from −714 to −1298. Rosemblit et al., 1996,*J. Endocrinology* 16(3):287-296. The human clusterin gene promoter region has been published. Michel et al., 1997 *Biochein. J.* 328:45-50; Wong et al. 1994 *Eur. J. Biochem* 221:917-925. Between mammalian clusterin promoters, a relatively modest conservation exists; most of the homology is confined within a very proximal domain with upstream regions being completely divergent. Michel, supra.

The promoter from the FSH receptor (FSHR) gene may also be used in the expression vectors of the present invention. FSHR gene expression is limited to Sertoli cells of the testis and granulosa cells of the ovary. Gromoll et al., 1996 *Genomics* 35:308-311. Thus, this tissue specific promoter is highly useful for the compositions and methods of the present invention. The FSHR gene has been isolated and characterized in mouse, rat and human. Goetz et al., 1996 *J. Biol. Chem.* 271(52):33317-33324. In rat, primer extension and S1 nuclease experiments have located two major transcriptional start sites; one at −80 and one at −98 relative to the translational start site. Transient expression studies utilizing a chimeric gene constituting 830 bp of DNA 5' to the translational start site operably linked to the cloramphenicol acetyltransferase (CAT) gene have demonstrated that this portion of the gene acts as transcriptional promoter in rat Sertoli cells. Heckert, L. L, et al., 1992 *Mol. Endocrin.* 6(1):70-80.

The human FSHR gene is 54 kb, consisting of 10 exons and 9 introns. The gene encodes 695 amino acids including a signal peptide of 18 amino acids. The core promoter region is located between the translational start codon and 225 bp upstream. As in rat and mouse, in the human gene, a consensus CAAT or TATA box is not located within this promoter region. Gromoll et al., supra. The promoter region of the human FSHR gene has been finely mapped and been shown to consist of a conserved consensus E box sequence and an initiator-like region (InR) sequence. A 114-base pair region spanning −143 to −30 which encompasses the E box and InR has been demonstrated as sufficient for conferring greater than 75% promoter function. Mutations in the InR, however, result in significant reduction of FSHR promoter activity. Goetz, supra. The sequence of the 5' flanking region of human FSHR gene has also been published. When transiently transfected with gene constructs containing 1486 bp of the 5' flanking region the FSHR gene (including deletions thereof), operably linked to the CAT gene, Chinese hamster ovary (CHO), primary rat Sertoli cells, and human granulosa-lutein cells directed significant expression of CAT. The promoter proximal region has been allocated to the region from −225 to −1 bp. Gromoll et al., 1994 *Molecular and Cellular Endocrinology* 102:93-102.

Another regulatory sequence useful for the compositions and methods of the present invention includes the transferrin gene promoter. Transferrin, an iron-transport protein, is expressed at a high level in the liver but at lower levels in other organs such as the brain, Sertoli cells of the testis, mammary glands and fetal muscle. Sertoli cells synthesize and secrete testicular transferrin. Schaeffer et al., 1993 *J. Biol. Chem.* 268(31):23399-23408; Guillou et al., 1991 *J. Biol. Chem.* 266(15):9876-9884; Skinner et al. 1980 *J. Biol. Chem.* 255: 9523-9525. The human gene has been isolated and the regulatory sequences identified. Adrian et al., 1986 *Gene* 49:167-175. 5'-deletion analysis in transient expression systems have indicated the region of −125/+39 as the promoter proximal region. Schaeffer et al., 1989 *J. Biol. Chem.* 264:7153-7160. The region spanning −52 to +30 TATA box is sufficient to activate a basal level of transcription. Guillou et al., 1991 *J. Biol. Chem.* 266:9876-9884. Transcriptional activation in Sertoli cells involves the interaction of DNA-binding proteins with the PRI-TATA box couple or the PRI-PRII couple. Guillou et al., 1991 *J. Biol. Chem.* 266:9876-9884. The transferrin promoter has also been found to contain two critical response elements designated Sertoli element 1 (SE1) and Sertoli Element 2 (SE2). Through sequencing analysis, SE2 has been found to contain an E-box element. E-box response elements have been demonstrated to respond to basic-helix-loop-helix (bHLH) transcription factors. bHLH transcription proteins are a class of transcription factors which are involved in the induction and progression of cell differentiation. Chaudhary, J., et al., 1997 *Endocrinology* 138(2):667-675.

Transgenic mice transformed with genetic constructs in which a 670-bp segment of the regulatory sequence from the human transferrin gene operably linked to the CAT gene or three different apolipoprotein E (apoE) alleles have exhibited expression of such genes in different portions of their brain. Bowman, B. H., et al., 1995 *Proc. Nat., Acad. Sci. USA* 92(26):12115-12119. The 5' flanking region of the mouse transferrin gene has also been isolated and used to drive expression of human growth hormone (hGH) in transgenic mice.

Those skilled in the art are familiar with the methodologies required to subclone all or a portion of the clusterin, FSHR, and transferrin genes, and to isolate the respective regulatory regions such as the promoter and 5' and 3' regulatory sequences. For example, a clusterin, FSHR, or transferrin gene promoter and upstream regulatory sequences may be generated from a mouse, rat, bovine, porcine, or human genomic clone having either or both excess 5' flanking sequence or downstream coding sequence via exonuclease III-mediated deletion. This is accomplished by digesting appropriately prepared DNA with exonuclease III (exoIII) and removing aliquots at increasing intervals of time during the digestion. The resulting successively smaller fragments of DNA may be sequenced to determine the exact endpoint of the deletions. There are several commercially available systems which use exonuclease III (exoIII) to create such a deletion series, e.g., Promega Biotech, "Erase-A-Base" system. Alternatively, PCR primers can be defined to allow direct amplification of the desired promoters and 5' regulatory regions.

A clusterin, FSHR, or transferrin 3' regulatory sequence, including 3' termination sequence, may be isolated from a mouse, rat, bovine, porcine, or human genomic clone having either or both excess 3' flanking sequence or upstream coding sequence via the same exoIII mediated deletion methodologies described above.

The 5' and 3' regulatory sequences and the DNA sequences which code for a desired protein and signal peptide can be modified for preparation of an expression vector by a variety of procedures. For example, the ends of the DNA prepared as described above can be ligated with the enzyme DNA ligase to short double-stranded DNA molecules which contain the nucleotide sequence recognized by specific restriction endonucleases, so called linker molecules. Digestion of these molecules with a specific restriction endonuclease following the ligation will generate termini corresponding to the specified restriction endonuclease recognition site at the ends of the prepared DNA sequence.

Thus, the present invention also provides a recombinant expression vector comprising in the 5' to 3' direction: a promoter which functions in a Sertoli cell and coding sequence for a biological factor or intermediate. In another embodiment, a subject vector comprises in the 5' to 3' direction: a promoter which functions in a Sertoli cell, coding sequence for a biological factor or intermediate and a 3' regulatory sequence including a termination sequence. In yet another embodiment, a vector is provided comprising in the 5' to 3' direction: a promoter which functions in a Sertoli cell, a signal sequence, and coding sequence for a biological factor or intermediate. In still another embodiment, there is provided a vector which comprises in the 5' to 3' direction: a promoter which functions in a Sertoli cell, a signal sequence, coding sequence for a biological factor or intermediate, and a 3' regulatory sequence including a termination sequence. Other embodiments include any of the above delineated vectors with additional 5' regulatory sequence in addition to the promoter.

The subject vectors may then be introduced into the Sertoli cell. The introduction of DNA into Sertoli cells can be accomplished through various well known procedures. For example, the subject vectors may comprise viral sequences required for packaging, reverse transcription, and integration into a host genome in addition to a promoter which functions in Sertoli cells operably linked to coding sequence for a biological factor or intermediate as described supra. Vectors having such sequences are useful for transfecting into helper cells from which recombinant virions can be produced. Virions containing the subject vectors are then used to transfect Sertoli cells.

Physical/chemical techniques such as calcium phosphate transfection, complex formation with polycations or lipids, electroporation, particle bombardment and microinjection into nuclei may also be used to transfect Sertoli cells. Preferably, the introduction of the subject vectors into Sertoli cells is accomplished using liposomes.

Lipofectin reagents are commercially available, e.g., the LipofectAMINE® system available from Gibco/BRL. In this methodology, positively charged and neutral lipids form liposomes that complex with the subject negatively charged DNA vector constructs. The DNA-liposome complexes are applied to the primary or cultured Sertoli cells and are taken up by endocytosis. The endosomes undergo breakage of membranes and the DNA constructs are released within the Sertoli cells. The DNA enters the nucleus of the Sertoli cell through nuclear pores and facilitates integration or homologous recombination into the chromosomes of the Sertoli cell.

After transfer of the genetic construct into Sertoli cells, cells are selected using the appropriate antibiotic. Detection of the expression of the heterologous gene is then performed using an appropriate assay. The assay used to detect expression depends of the nature of the heterologous sequence. For example, reporter genes exemplified by chloramphenicol acetyl transferase (CAT), β-galactosidase and luciferase, are commonly used to assess transcriptional and translational competence of chimeric constructions. Standard assays are available to sensitively detect the reporter enzyme in a transgenic organism. For example, a CAT assay may be employed which detects mono and diacetylated chloramphenicol derivatives by thin layer chromatography. The chloramphenicol derivatives may be quantitated by phosphor imaging.

Sertoli cells transformed with vectors comprising the reporter gene, β-galactosidase, can be identified by detecting the cleaved galactosidase moiety by light emission. This method is best performed using a luminometer or scintillation counter.

The introduction of Sertoli cells genetically altered to produce a desired biological factor or intermediate into a subject such as a mammal is accomplished by conventional techniques. In a preferred embodiment, introduction is by subcutaneous transplantation. Examples of preferred locations for transplantation include the renal subcapsular space, liver subcapsular space, omental pouch, subcutaneous facie, the brain and the hepatic portal vein. Immunoprivileged environments may be created at the site of transplantation using either allogeneic or xenopeneic Sertoli cells.

In accordance with the present invention, an exogenous biological factor may be administered following the transplantation of the genetically altered Sertoli cells until the transplanted Sertoli cells produce a therapeutically effective amount of the biological factor. For example, in the treatment of diabetes, insulin may be administered following the transplantation of insulin-producing Sertoli cells until the transplanted Sertoli cells produce a therapeutically effective amount of insulin.

The Sertoli cells which produce the biological factor or intermediate can be transplanted using any technique capable of introducing the cells into a subject such as parenteral administration or subcutaneous administration following surgical exposure to a desired site. Prior to transplantation, the recipient mammal is anesthetized using local or general anesthesia according to conventional techniques. For example, after the mammal is anesthetized, the Sertoli cells can be injected into a tissue mass, thereby creating an immunoprivileged site. In a preferred embodiment, the subject to be treated is a mammal. In an even more preferred embodiment, the mammal is a human.

In accordance with the present invention, introduction of Sertoli cells genetically altered to produce a biological factor or intermediate also results in the creation of an immunologically privileged site in the treated subject. An immunologically privileged site as defined by the present invention is a site in the subject where the immune response produced in response to the transplanted cells is suppressed due to immuno-suppressive agents produced by the transplanted Sertoli cells.

As used herein, the term "allogeneic" refers to tissues or cells of two genetically dissimilar subjects of the same species. The term "xenogeneic" refers to tissues or cells of two genetically dissimilar subjects of different species. The term "allograft" as used in the present invention describes the transfer of tissues or cells between two genetically dissimilar subjects of the same species. The term "xenograft" in the present invention describes the transfer of tissues or cells between two subjects of different species.

Sertoli cells are introduced in an amount effective to provide an immunologically privileged site. Such an effective amount is defined as that which prevents immune rejection of the transplanted, genetically altered Sertoli cells. Immune rejection can be determined for example histologically, or by functional assessment of the biological factor produced by the cells.

The genetically altered Sertoli cells producing the biological factor are introduced in a therapeutically effective amount. By "therapeutically effective amount" is meant an amount effective to produce the desired effect. For example, in the case of a peptide which stimulates the appetite, a therapeutically effective amount is an amount which stimulates the appetite. In the case of a peptide which depresses the appetite, a therapeutically effective amount is an amount which depresses the appetite. In the case of a particular disease, "a therapeutically effective amount" is that amount effective to treat the disease. For purposes of the present invention, the terms "treat" or "treatment" include preventing, inhibiting, reducing the occurrence of and/or ameliorating the physiological effects of the disease condition treated.

The ordinary skilled artisan can determine the appropriate amount of cells producing the biological factor or intermediate by methods known in the art. The amount of Sertoli cells is dependent upon the amount of factor being produced by the cells and the known therapeutically effective amount of the factor necessary to produce the desired effect or treat the disease. The precise therapeutically effective amount of genetically altered Sertoli cells can be determined by a physician with consideration of individual differences in age, weight, the particular disease to be treated, stage of the disease, and condition of the patient. It can generally be stated that a therapeutic composition comprising the subject genetically altered Sertoli cells should be preferably administered in an amount of at least about $1 \times 10^1$ to about $1 \times 10^{10}$ cells per dose.

After transplantation of the genetically altered Sertoli cells producing a biological factor or intermediate, an immunosuppressive agent may be administered for such a time during which the Sertoli cells become established and create the immunoprivileged site. Such immunosuppressive agents include for example, cyclosporine, tacrolimus, despergualin and monoclonal antibodies to, e.g., T cells. In a preferred embodiment the immunosuppressive agent is cyclosporine. In another preferred embodiment cyclosporine is administered at a dosage of from 0.5 mg to 200 mg/kg body weight. In a most preferred embodiment cyclosporine is administered at a dosage of from 5 mg to 40 mg/kg body weight.

More generally, the immunosuppressive agent can be administered for a time sufficient to permit the transplanted Sertoli cells become functional. This period extends from the point prior to or immediately following the transplantation of the Sertoli cells to the point at which the cells are capable of producing therapeutically effective amounts of the biological factor or intermediate. In a preferred embodiment, the sufficient period of time to administer an immunosuppressive agent is about 40 to about 100 days following transplantation of the Sertoli cells. In a more preferred embodiment, the sufficient period of time is about 50-60 days.

One embodiment of this invention is directed to a method of treating Type I and Type II diabetes mellitus by transplanting into the renal subcapsular space, Sertoli cells which have been genetically altered to produce insulin. In another embodiment of the invention, there is provided a method of treating hemophilia B by transplanting into the renal subcapsular space, Sertoli cells which have been genetically altered to produce Factor IX. In still another embodiment of the invention, there is provided a method of treating Crigler-Najjar (CN) disease by transplanting into the renal subcapsular space, Sertoli cells which have been genetically altered to produce bilirubin UDP-glucuronosyltransferase (B-UGT).

Another aspect of the present invention provides a pharmaceutical composition comprising Sertoli cells genetically altered to produce a biological factor or intermediate and a pharmaceutically acceptable carrier. In a preferred embodiment, the Sertoli cells are rat, murine, porcine, bovine or human Sertoli cells. As used herein, a pharmaceutically acceptable carrier includes any and all solvents, dispersion media, coatings, antibacterial and antifungal agents, isotonic agents and the like. The use of such media and agents is well-known in the art.

The present invention is also directed to a kit for treatment of a disease. In one embodiment, the kit is compartmentalized to receive a first container adapted to contain Sertoli cells genetically altered to produce a biological factor or intermediate thereof that is absent, produced at low levels, or defective in the individual to be treated in an amount effective to produce the desired effect or treat the disease. In a preferred embodiment, the Sertoli cells are rat, murine, bovine, porcine or human and are provided in an amount of from $10^1$ to $10^{10}$ cells. In a more preferred embodiment, Sertoli cells are provided in an amount of from $10^5$ to $10^{10}$ cells. In another preferred embodiment the Sertoli cells that produce a biological factor or intermediate are cells that have been transformed with DNA encoding the factor or intermediate.

The invention is further illustrated by the following specific examples which are not intended in any way to limit the scope of the invention.

EXAMPLE 1

Sertoli cells are isolated from Lewis rats and cultured for two to seven days using standard techniques (Selawry, H. P. and Cameron, D. F., 1993 *Cell Transplantation* 2:123-129; Korbutt, G. S., et. al., 1997 *Diabetes* 46:317-322). For example, testicles from 15 to 21-day-old Lewis rates are collected in Hanks' balanced salt solution (HBSS), chopped into 1-mm pieces with scissors, and digested for 10 minutes at 37° C. with collagenase (2.5 mg/ml; Sigma Type V, St. Louis, Mo.) in HBSS. The digest is washed three times with calcium- and magnesium-free HBSS containing 1 mmol/EDTA and 0.5% bovine serum albumin (Sigma)(HBSS/EDTA), digested for 10 minutes at 37° C. with trypsin (25 µg; Boehringer) in HBSS/EDTA, and washed four times in HBSS; the final cell pellet is resuspended in HAM's F10 media supplemented with 10 mmol/l D-glucose, 2 mmol/l L-glutamine, 50 µmol/l isobutylmethylxanthine, 0.5% bovine serum albumin, 10 mmol/l nicotinamide, 100 U/ml penicillin, 100 ng/ml streptomycin, and 5% Lewis rat serum (not heat inactivated). The tissue is passed through a 500-µm mesh, placed in non-tissue culture-coated Petri dishes and incubated for 48 hours at 37° C. (5% $CO_2$) before transplation.

An expression vector containing the CMV promoter and the gene for β-galactosidase is used to transfect the Sertoli cells. For example, pCMVbeta (available from Clontech, Palo Alto, Calif.) contains the human cytomegalovirus early gene promoter, an intron (splice donor/splice acceptor) and polyadenylation signal from SV40 along with the full-length *E. coli* beta-galactosidase gene with eukaryotic translation signals. Alternatively, an expression vector constituting the chloramphenicol acetyltransferase gene (CAT) under control of the SV40 promoter (pCAT3, available from Promega, Madison, Wis.) is used to transfect the Sertoli cells.

After about two to seven days in culture, the Sertoli cells are transfected using the lipofectin method of Gibco/BRL (Rockville, Md.) and following the instructions provided by the manufacturer. The calcium phosphate method coupled with hyperosmotic shock (10% glycerol) as described in Whaley et al. (1995) *Endocrinology* 136:3046-3053, may also be used.

Following transfection, in order to select those Sertoli cells transformed by an expression vector, an appropriate assay is employed. For example, Sertoli cells transfected with the CAT gene undergo a CAT assay which detects mono and diacetylated chloramphenicol derivatives such as the assay described in Gorman et al., (1982) *Mol. Cell. Biol.* 2(9):1044-1051. The chloramphenicol derivatives may be quantitated by phosphor imaging.

Sertoli cells transfected with the lacZ gene are identified by detecting the cleaved galactosidase moiety using light emission. A luminometer or scintillation counter is best suited for this purpose. Transfected Sertoli cells are plated at $5 \times 10^5$ cells per plate. Cells are plated in triplicate and expression is assayed at 0, 2, 4, 8, 12, 18, 28 and 42 days. If expression is lower than expected, the expression vector may be altered by incorporating the PCAT enhancer.

After selection of cells with stable integration of the genetic construct, the selected cells are allowed to expand in culture (about 15-21 days) After expansion, the cells are collected for transplantation.

EXAMPLE 2

The collected Sertoli cells from Example 1 are then pooled and transplanted in a normal rat under the kidney (renal) sub-capsular space. The transplantation protocol used to transplant the stably transfected cells is the same as that used for transplantation of islet cells and Sertoli cells described in Rajotte et al. (1997) *Diabetes* 46:317-322. For example, each recipient receives between about $5.5 \pm 0.3$ to $11 \pm 0.4 \times 10^6$ transgenic Sertoli cells. Cells are aspirated into polyethylene tubing such as PE-50, pelleted by centrifugation, and gently placed under the left renal subcapsular space of anesthetized (e.g., halothane-anesthetized) animals. The number of transgenic Sertoli cells grafted in each animal is assessed by measuring the DNA content of triplicate representative aliquots of each cell preparation before transplantation, and calculations are based on the finding that freshly isolated testicular cells contain about 20 pg DNA per cell. Therefore, the total DNA content transplanted per 20 pg DNA per testicular cells equals the testicular cell number.

A predetermined number of rats undergo transplantation with the genetically altered Sertoli cells. Both isografts (Lewis rat transformed Sertoli cells transplanted into Lewis rats) and allografts (Lewis rat transformed Sertoli cells transplanted into Wistar-Furth rats) are performed. As controls, Lewis rats receive both isografts and allografts of untransformed Sertoli cells transplanted under the kidney capsule. Also as a control, islets isolated from Lewis rat pancreatic tissue is transplanted into Wistar-Furth recipients.

A portion of the rats with transplanted Sertoli cells are sacrificed for histological examination at various time points post-transplantation. The time points post-transplantation are approximately 5, 10, 15, 20, 30, 50 and 90 days. The histological examination is performed in triplicate at each time point.

Kidney tissue containing the different grafts is examined histologically using immunohistochemical staining e.g. for clusterin, to ensure that the Sertoli cells are still viable, i.e, have not been rejected, and that β-galactosidase continues to be produced.

EXAMPLE 3

Lewis rat Sertoli cells are transfected with a retroviral vector constituting the alkaline phosphatase gene. The RetroExpress® system, available from Clontech is especially useful. After selection and expansion as described in Example 2, transfected Sertoli cells are transplanted into Wistar-Furth rats as described in Example 2.

EXAMPLE 4

Porcine Sertoli cells are isolated similarly to the methods described in Korbutt et al. (1997) *Diabetes* 46:317-322 and Selawry (1993) *Cell Transplantation* 2:123-129. Testes are removed from recently expired pigs with scissors and forceps. The testes are placed in a beaker containing approximately 100 ml Hank's Balanced Salt Solution plus $CaCl_2$ (HBSS, Life Technologies), supplemented with an antibiotic such as gentamycin.

A piece of testicular tissue is removed from the testes. The tunica albugeia is removed from the tissue leaving a smaller aliquot of about 1.45 to 1.63 g. The parenchyma is minced with scissors and between about 1.45 and 1.63 g of testis is placed in a 50 ml centrifuge tube and the sample is washed by centrifugation twice with Hank's+$CaCl_2$. The total volume for each wash is between 35 to 40 ml and the sample is centrifuged at 1000 rpm for about three minutes.

30 ml of Hank's plus CaCl2 is added to the pellet followed by 33 mg of collagenase. The sample and media are transferred to a flask, capped with sterile gauze and foil, and placed in a shaker/water bath at 37° C. for 15 minutes (shaker setting approximately 6.5). Cells are transferred to a 50 ml centrifuge tube and washed two times with Hank's plus $CaCl_2$. To the cells are added 400 μl trypsin(stock solution of 2. mg/ml), 200 μl DNase (stock solution of 1 mg/ml), 40 ml of Hank's (WITHOUT Calcium or Magnesium, Life Technologies). The cells and media are transferred to a flask and placed in a shaking water bath for ten minutes at 37° C. Cells and media are then transferred to a 50 ml centrifuge tube and washed three times with Hank's plus CaCl2. After the final wash, 20 ml of Media 199 (Sigma Biosciences, St. Louis, Mo.) plus 5% Horse Serum plus antibiotics [herein referred to as "Media 199"] is added to the tube, the pellet resuspended and the suspension poured through a 500 micron cell collector into a beaker. An additional 10 ml of Media 199 is poured over the cells. Passing of the cells is facilitated by gently pushing with the plunger of a 10 ml syringe. An additional 10 ml of Media 199 is poured over the cells and the process repeated. The cells are diluted further with another 10 ml of Media 199 (total volume=50 ml). At this point, a sample may be placed under a phase/contrast microscope to confirm the predominance and integrity of Sertoli cells in the preparation.

In order to estimate cell number based on correlation to DNA content (see Example 2), 2 ml of cell suspension is removed to a small plastic centrifuge tube, centrifuged at 2000 rpm for ten minutes, the media removed, and the resulting pellet, resuspended in the media remaining in the tube. The sample may be placed in a −50° C. freezer prior to DNA analysis.

To either non-stick Falcon 1001 plates or stick plates (Falcon 3003) is added 3 ml cell suspension and 12 ml Media 199. In addition, 0.2 ml of antibiotic/antimycotic was added to each plate. Plates are placed in an incubator at 37° C. and 2% $CO_2$. Cells are cultured for two to seven days.

Alternatively, the above-described method is altered as follows. After the step of adding 30 ml of Hank's+$CaCl_2$ to the minced testes parenchyma, instead of adding 33 mg of collagenase, 30 mg of trypsin (from 2 mg/ml stock) and 0.6 mg of DNase (from 1 mg/ml stock) is added and the suspension is transferred to a flask such as an Erlenmeier flask. The flask is placed in a shaking water bath for 30 minutes at 37° C. Following this step, the suspension is transfered to a 50 ml centrifuge tube and the cells are washed three times with Hank's+CaCl$_2$. Cells are resuspended in 40 ml of 1M glycine+2 mM EDTA containing 0.01% soy trypsin inhibitor+ 0.8 ml DNase. The suspension is incubated for ten minutes at room temperature. Following the incubation step, cells are washed three times by centrifugation with Hank's+CaCl$_2$. After the last centrifugation, cells are suspended in 40 ml of Hank's+CaCl$_2$+0.2 mg of DNase (1 mg/ml stock) and 40 mg collagenase. The suspension is transferred to a flask such as an Erlenmeir flask and shaken in a 37° C. waterbath for ten minutes. After transferring cells to a 50 ml centrifuge tube, cells are washed three times with Hank's. Thirty ml of Media 199 is added to the pellet and the cells are resuspended and poured through a 500 micron cell collector into a beaker. Passing of the cells is facilitated by gently pushing with the plunger of a 10 ml syringe. An additional 20 ml of Media 199 is poured over the cells and the process repeated. Cells are resuspended in a final volume of 50 ml and may be examined under a phase/contrast microscope for the presence and integrity of Sertoli cells.

For DNA content analysis, (see Example 2), 2 ml of cell suspension is removed to a small plastic centrifuge tube, centrifuged at 2000 rpm for ten minutes, the media removed and the resulting pellet, resuspended in the media remaining in the tube. The cells are stored in a −50° C. freezer.

Non-stick plates receive 5 ml of cells plus an additional 10 ml of Media 199. Stick plates receive 3 ml of cells and 12 ml of Media 199. All plates receive 0.2 ml of antibiotic/antimycotic and plates are incubated at 37° C. and 2% CO$_2$.

The porcine Sertoli cells are transfected via the Lipofectin method with the expression vectors as detailed in Example 1 or via the retroviral system described in Example 3. The transfected porcine Sertoli cells are transplanted to the renal subcapsular space of Wistar-Furth rats as described in Example 2. The grafts are assayed as described in Example 2.

EXAMPLE 5

Mouse, rat, and porcine Sertoli cells are genetically altered to express the human Factor IX gene. The constructs used to transfect the Sertoli cells contain the human Factor IX gene under the control of a promoter such as the CMV promoter, rat, mouse or porcine transferrin gene promoter, human transferrin gene promoter, rat, mouse or porcine FSHR gene promoter, and human FSHR gene promoter.

An expression vector comprising a promoter which functions in rat Sertoli cells is operably linked to the cDNA for human factor IX cDNA. Human factor IX cDNA is described in Palmer et al., 1989 *Blood* 73:438-445. Initially, the CMV promoter is employed. Transfected rat Sertoli cells are used for transplantation into normal rats (controls) and in factor IX deficient rats. A factor IX-deficient mouse model for hemophilia B gene therapy has been developed where the clotting factor IX (FIX) gene has been disrupted by homologous recombination. Wang, L. et al. 1997 *Proc. Natl. Acad. Sci U.S.A.* 94(21):11563-11566. The same experiment is repeated using pig Sertoli cells rather than rat Sertoli cells followed by transplantation into rats. In a third experiment, Sertoli dell-specific promoters such as those of the rat transferrin, clusterin, or FSH receptor genes operably linked to the cDNA for human factor IX are used to transfect rat Sertoli cells followed by transplantation into rats. In a fourth experiment, Sertoli cell-specific promoters such as those of the rat transferrin, clusterin, or FSH receptor genes operably linked to the cDNA for human factor IX are used to transfect porcine Sertoli cells followed by transplantation into rats.

After transplantation, the graft is examined at time intervals of 5, 10, 15, 20, 30, 50, and 90 days and assayed for factor IX production by immunohistochemistry as described in Wang, L., 1997 supra.

EXAMPLE 6

Gunn rats are incapable of bilirubin conjugation due to a genetic defect in UDP-glucuronyl transferase. As a result, Gunn rats may be used as a model of congenital enzymatic deficiency to test the metabolic activity of transplanted cells. Seppen J., et al., 1997 *Hum. Gene. Ther.* 8(1):27-36.

In this experiment, mouse, rat and porcine Sertoli cells are transfected with a gene construct having the bilirubin UDP-glucuronosyltransferase (B-UGT) gene (Seppen, J. 1997 supra) under the control of a promoter which functions in rats such as the rat transferrin, clusterin or FSH receptor genes and transplanted into Gunn rats.

After Sertoli cells expressing B-UGT are found to glucuronidate bilirubin present in cell culture media, the cells are transplanted under the kidney capsule and/or liver capsule of Gunn rats. Animals exhibiting a B-UGT deficiency corrected by the Sertoli cell transplantation are detected by the presence of normal serum bilirubin concentrations and bilirubin glucuronides in the bile.

What is claimed is:

1. A method for providing a subject with a protein which comprises introducing into the subject a therapeutically effective amount of primary Sertoli cells that have been genetically altered by ex vivo gene transfer to produce said protein or isolated from a non-human transgenic animal that has been genetically altered to produce said protein, and wherein said Sertoli cells create an immunologically privileged site.

2. A method of treating a disease that results from a deficiency of a protein which comprises introducing into a subject in need of such treatment, a therapeutically effective amount of primary Sertoli cells that have been genetically altered by ex vivo gene transfer to produce said protein or isolated from a non-human transgenic animal that has been genetically altered to produce said protein, and wherein said Sertoli cells create an immunologically privileged site.

3. The method of claim 1 or 2 wherein said subject is a mammal.

4. The method of claim 3 wherein said mammal is human.

5. The method of claim 1 or 2 wherein said protein is a hormone.

6. The method of claim 3 wherein said protein is a hormone.

7. The method of claim 2 wherein said protein is insulin and said disease is diabetes mellitus.

8. The method of claim 2 wherein said protein is Factor IX and said disease is hemophilia B.

9. The method of claim 2 wherein said protein is B-UGT and said disease is Crigler-Najjar (CN) disease.

10. The method of claim 1 or 2 wherein said introduction is by transplantation.

11. The method of claim 1 or 2 wherein said Sertoli cells are introduced into said individual in a dosage ranging from $10^5$ to $10^{10}$ cells.

12. The method of claim 10 wherein said transplantation is by xenograft.

13. The method of claim 10 wherein said transplantation is by allograft.

14. The method according to claim 1 or 2, wherein said Sertoli cells are isolated from a non-human transgenic animal and express said protein.

15. The method of claim 1 or 2, wherein said Sertoli cells are rat, murine, porcine, or bovine.

16. The method of claim 15, wherein said Sertoli cells are isolated from a transgenic mouse.

17. The method of claim 1 or 2, wherein said Sertoli cells have been genetically altered by ex vivo gene transfer to produce said protein.

18. The method of claim 1 or 2, wherein the subject is human and said Sertoli cells are xenogeneic.

* * * * *